US012626787B2

(12) United States Patent
Kwon et al.

(10) Patent No.: US 12,626,787 B2
(45) Date of Patent: May 12, 2026

(54) METHOD AND APPARATUS FOR GENERATING NEW CHEMICAL STRUCTURE USING NEURAL NETWORK

(71) Applicant: SAMSUNG ELECTRONICS CO., LTD., Suwon-si (KR)

(72) Inventors: Youngchun Kwon, Yongin-si (KR); Jiho Yoo, Hwaseong-si (KR); Younsuk Choi, Seongnam-si (KR); Youngmin Nam, Seoul (KR); Minsik Park, Hwaseong-si (KR); Jinwoo Park, Suwon-si (KR); Dongseon Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1142 days.

(21) Appl. No.: 17/114,713

(22) Filed: Dec. 8, 2020

(65) Prior Publication Data

US 2021/0174910 A1     Jun. 10, 2021

(30) Foreign Application Priority Data

Dec. 9, 2019     (KR) ........................ 10-2019-0162918

(51) Int. Cl.

| | |
|---|---|
| *G16C 20/50* | (2019.01) |
| *G06N 3/02* | (2006.01) |
| *G06N 3/04* | (2023.01) |
| *G06N 3/08* | (2023.01) |
| *G16C 20/70* | (2019.01) |

(52) U.S. Cl.
CPC .............. *G16C 20/50* (2019.02); *G06N 3/02* (2013.01); *G06N 3/04* (2013.01); *G06N 3/08* (2013.01); *G16C 20/70* (2019.02)

(58) Field of Classification Search
CPC ........ G16C 20/50; G16C 20/70; G16C 20/10; G16C 60/00; G16C 20/60; G06N 3/02; G06N 3/04; G06N 3/08; G06N 3/044; G06N 3/045; G06N 3/048; G06N 3/047; G06N 3/088
See application file for complete search history.

(56) References Cited

U.S. PATENT DOCUMENTS

| | | | |
|---|---|---|---|
| 10,436,713 | B2 | 10/2019 | Battrell et al. |
| 2015/0310162 | A1 | 10/2015 | Okuno et al. |
| 2017/0124482 | A1 | 5/2017 | Yoo et al. |
| 2017/0161635 | A1 | 6/2017 | Oono et al. |
| 2018/0012124 | A1 | 1/2018 | Hara et al. |
| 2019/0220573 | A1 | 7/2019 | Kwon et al. |
| 2019/0287012 | A1 | 9/2019 | Celikyilmaz et al. |
| 2019/0355444 | A1 | 11/2019 | Yoo et al. |

FOREIGN PATENT DOCUMENTS

| | | |
|---|---|---|
| CN | 110046692 A | 7/2019 |
| EP | 3 514 734 A1 | 7/2019 |
| JP | 2019-502988 A | 1/2019 |
| JP | 2019-86817 A | 6/2019 |
| KR | 10-2015-0097764 A | 8/2015 |
| KR | 10-2017-0052344 A | 5/2017 |
| KR | 10-2019-0087898 A | 7/2019 |
| KR | 10-2019-0132169 A | 11/2019 |

OTHER PUBLICATIONS

Gómez-Bombarelli R. Design of efficient molecular organic light-emitting diodes by a high-throughput virtual screening and experimental approach. Nature Materials 15: 1120-1129. (Year: 2016).*
Gómez-Bombarelli et al., "Automatic Chemical Design Using a Data-Driven Continuous Representation of Molecules," ACS Central Science vol. 4, No. 2, pp. 268-276, Jan. 2018, XP055589835 (total 9 pages).
Kim et al., "Deep-learning-based inverse design model for intelligent discovery of organic molecules," npj Computational Materials, vol. 4, No. 1, Dec. 2018, XP055633998 (total 7 pages).
Kwon et al., "Efficient learning of non-autoregressive graph variational autoencoders for molecular graph generation," Journal of Cheminformatics, vol. 11, No. 1, Nov. 2019, XP055798430 (total 10 pages).
Schroedl, "Current methods and challenges for deep learning in drug discovery," Elsevier, Drug Discovery Today: Technologies, vol. 32, pp. 9-17, Dec. 2019, XP086429569 (total 9 pages).
Chang, "Probabilistic Generative Deep Learning for Molecular Design," arXiv.org, Cornell University Library, Feb. 2019, XP081028929 (total 17 pages).
Communication dated May 7, 2021, issued by the European Patent Office in counterpart European Application No. 20211499.7.
Rafael Gómez-Bombarelli et al., "Automatic Chemical Design Using a Data-Driven Continuous Representation of Molecules", arXiv: 1610.02415v3 [cs.LG] Dec. 5, 2017 (Total 26 pages).
Office Action issued Dec. 10, 2024 by Japanese Patent Office in Japanese Patent Application No. 2020-202914.
Communication issued on Jul. 22, 2025 by the Korean Intellectual Property Office in Korean Patent Application No. 10-2019-0162918.
Office Action issued on Nov. 27, 2025 by the Chinese Patent Office in corresponding CN Patent Application No. 202010959240.X.

* cited by examiner

*Primary Examiner* — Olivia M. Wise
*Assistant Examiner* — Robert J. Kallal
(74) *Attorney, Agent, or Firm* — Sughrue Mion, PLLC

(57) ABSTRACT

A neural network apparatus for generating a new chemical structure may receive a structure input of a chemical structure; generate, based on the structure input, a negative attention vector that indicates a respective probability of presence of each of a plurality of blacklists in the structure input; generate a structure expression by encoding the structure input; generate a final reverse blacklist vector that does not include the plurality of blacklists, based on the negative attention vector and the structure expression; and generate the new chemical structure by decoding the final reverse blacklist vector.

15 Claims, 10 Drawing Sheets

INCLUDING RING STRUCTURE
WHICH IS AT MOST TETRAGONAL

AT LEAST SIX O

INCLUDING ELEMENTS
OTHER THAN C, O, AND N

INCLUDING RING STRUCTURE
WHICH IS AT LEAST HEPTAGONAL

METHOD AND APPARATUS FOR GENERATING NEW CHEMICAL STRUCTURE USING NEURAL NETWORK

CROSS-REFERENCE TO RELATED APPLICATION

This application is based on and claims priority under 35 U.S.C. § 119 to Korean Patent Application No. 10-2019-0162918, filed on Dec. 9, 2019, in the Korean Intellectual Property Office, the disclosure of which is incorporated by reference herein in its entirety.

BACKGROUND

1. Field

The present disclosure relates to an apparatus and method for generating a new chemical structure.

2. Description of Related Art

Neural networks refer to a computational architecture in which a biological brain is modeled. With the development of neural network technology, neural networks have been used in various types of electronic systems to analyze input data and extract effective information.

Recently, research has been actively carried out to evaluate properties of chemical structures by using neural network technology so as to select chemical structures to be used for developing materials. According to a method of designing a material using neural network technology according to the related art, it is checked ex post facto whether or not a new chemical structure includes predetermined blacklists after obtaining the new chemical structure, and thus such a new chemical structure including the blacklists is filtered.

However, most new chemical structures generated using a neural network model include the blacklists, and thus, it is difficult to obtain new chemical structures having satisfactory properties.

SUMMARY

Provided are apparatuses and methods for generating a chemical structure using a neural network. Provided is a computer-readable recording medium in which a program for executing the method on a computer is recorded. Technical problems to be solved are not limited to the above technical problems, and thus other technical problems may exist.

Additional aspects will be set forth in part in the description which follows and, in part, will be apparent from the description, or may be learned by practice of the presented embodiments of the disclosure.

According to an aspect of an embodiment, a method of generating a new chemical structure may be performed by a neural network apparatus and may include receiving a structure input; generating, based on the structure input, a negative attention vector that indicates a respective probability of presence of each of a plurality of blacklists in the structure input; generating a structure expression by encoding the structure input; generating a final reverse blacklist vector that does not include the plurality of blacklists, based on the negative attention vector and the structure expression; and generating the new chemical structure by decoding the final reverse blacklist vector.

The method may include calculating a reverse negative attention vector using the negative attention vector, and generating of the final reverse blacklist vector may include generating the final reverse blacklist vector based on the reverse negative attention vector and the structure expression.

The method may include generating a final blacklist vector that includes the plurality of blacklists based on the negative attention vector and the structure expression during a learning process of a chemical structure generation model; and training the chemical structure generation model based on the new chemical structure and a blacklist prediction result corresponding to the new chemical structure.

The method may include calculating the blacklist prediction result using a non-negative parameter.

The structure input may include chemical structures confirmed not to include at least a part of the plurality of blacklists during a learning process of a chemical structure generation model.

The method may include selecting a part of the plurality of blacklists. The generating of the negative attention vector may include generating, based on the structure input, the negative attention vector in which the respective probability of presence of each of the selected blacklists in the structure input is indicated, and the generating of the final reverse blacklist vector may include generating the final reverse blacklist vector that does not include the selected blacklists based on the negative attention vector and the structure expression.

The generating of the final reverse blacklist vector may include generating the final reverse blacklist vector based on an element-wise multiplication between the reverse negative attention vector and the structure expression.

The method may include generating, based on the structure input, a positive attention vector that indicates a respective probability of presence of each of a plurality of whitelists in the structure input; generating a final whitelist vector including the plurality of whitelists based on the positive attention vector and the structure expression; and generating the new chemical structure by decoding the final whitelist vector.

The structure input may include chemical structures confirmed to include at least a part of the plurality of whitelists during a learning process of a chemical structure generation model.

The structure input may include chemical structures confirmed not to include at least a part of the plurality of blacklists, and confirmed to include at least a part of the plurality of whitelists during a learning process of a chemical structure generation model.

According to an aspect of an embodiment, a neural network apparatus for generating a new chemical structure may include a memory in which at least one program is stored; and a processor configured to execute the at least one program to: receive a structure input of a chemical structure; generate, based on the structure input, a negative attention vector that indicates a respective probability of presence of each of a plurality of blacklists in the structure input; generate a structure expression by encoding the structure input; generate a final reverse blacklist vector that indicates portions not corresponding to the plurality of blacklists, based on the negative attention vector and the structure expression; and generate the new chemical structure based on the final reverse blacklist vector.

According to an aspect of an embodiment, a non-transitory computer-readable medium may store a program that, when executed by a neural network apparatus, cause the neural network apparatus to: receive a structure input of a chemical structure; generate, based on the structure input, a negative attention vector that indicates a respective probability of presence of each of a plurality of blacklists in the structure input; generate a structure expression by encoding the structure input; generate a final reverse blacklist vector that does not include the plurality of blacklists, based on the negative attention vector and the structure expression; and generate the new chemical structure by decoding the final reverse blacklist vector.

According to an aspect of an example embodiment, a method of generating a new chemical structure may include receiving an input of a chemical structure; generating, based on the input, a first vector having n values that correspond to n blacklisted partial structures, and that respectively identify a probability of presence of each of the blacklisted partial structures in the chemical structure; generating a structure expression by encoding the input; generating a second vector that does not include the blacklisted partial structures, based on the first vector and the structure expression; and generating the new chemical structure by decoding the second vector.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
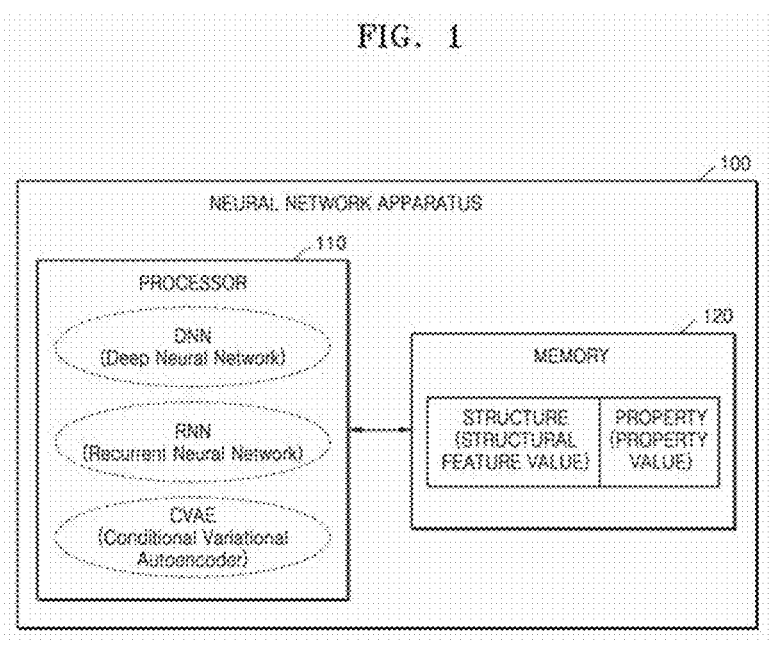
FIG. 1 is a block diagram illustrating a hardware configuration of a neural network apparatus according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

The terms "in some embodiments" and "in an embodiment" used herein do not necessarily indicate the same embodiment.

Some embodiments of the present disclosure may be represented by functional blocks and various processing operations. Some or all of such functional blocks may be implemented as various numbers of hardware and/or software components for performing specific functions. For example, the functional blocks of the present disclosure may be implemented using one or more microprocessors, or may be implemented using circuits for predetermined functions. Furthermore, for example, the functional blocks of the present disclosure may be implemented with various programming or scripting languages. The functional blocks may be implemented as algorithms to be executed by one or more processors. Furthermore, the present disclosure may employ typical technologies for electronic environment setting, signal processing, and/or data processing. The terms such as "mechanism," "element," "means," "configuration," and the like, may be widely used herein, and are not limited to mechanical and physical configurations.

Furthermore, the connection lines or connection members between elements illustrated in the drawings are merely examples of functional connections and/or physical or circuit connections. In actual applications, they may be replaced or embodied as various additional functional connections, physical connections, or circuit connections.

Regarding the terminology used herein, a descriptor, which is data used in a neural network system, is an index value used for expressing features of materials, and may be obtained by performing relatively simple computational processing with respect to a given material. In an embodiment, the descriptor may include a quantitative structure-property relationships (QSPR) descriptor including immediately calculable values such as a molecular weight or the number of partial structures (e.g., rings) included in a molecular structure or a molecular structure fingerprint (e.g., Morgan fingerprint or extended connectivity fingerprint (ECFP)) indicating whether a particular partial structure is included.

Furthermore, the term "property" represents characteristics of a material, and may include a real number value measured through an experiment or calculated through a simulation. For example, the property may be a transmission wavelength, a light emission wavelength, or the like, related to light when the material is a display material, or the property may be a voltage when the material is a battery material. Unlike the descriptor, the property may require a complex simulation and a long time in order to be calculated.

Furthermore, the term "structure" represents an atomic-level structure of a material. Since it may be required to express a structure in an atomic level in order to derive the property by performing first principles calculation, the structure of a material may be required to be derived in an atomic level so as to generate a new chemical structure. The structure may include a structural formula based on a bond between atoms, or may include a character string (one dimensional) having a simple format. A character string format for expressing the structure may include a simplified molecular-input line-entry system (SMILES) code, a smiles arbitrary target specification (SMARTS) code, or an international chemical identifier (InChi) code.

Furthermore, the term "factor" represents an element defining a relationship between the descriptor, the property, and the structure. The factor may be determined by performing machine learning on the basis of a descriptor-property-structural formula relationship stored in a database. Accordingly, it may be detected how the factor is connected to the descriptor, the property, and the structural formula.

Hereinafter, embodiments of the present disclosure will be described in detail with reference to the accompanying drawings.

FIG. 1 is a block diagram illustrating a hardware configuration of a neural network apparatus according to an embodiment.

A neural network apparatus 100 may be implemented as various types of devices such as a personal computer (PC), a server device, a mobile device, an embedded device, and the like, and, for example, may correspond to, but is not limited to, a smartphone, a tablet device, an augmented reality (AR) device, an Internet of things (IoT) device, an autonomous vehicle, a robotic device, a medical device, and the like, which performs voice recognition, image recognition, image classification, and the like, using a neural network. Furthermore, the neural network apparatus 100 may correspond to a dedicated hardware (HW) accelerator installed in the above devices, and the neural network apparatus 100 may include, but is not limited to, a hardware accelerator such as a neural processing unit (NPU), a tensor processing unit (TPU), a neural engine, and the like, which are dedicated modules for operating a neural network.

Referring to FIG. 1, the neural network apparatus 100 includes a processor 110 and a memory 120. FIG. 1 illustrates components of the neural network apparatus 100 related to the present embodiments. Therefore, it should be obvious to those of ordinary skill in the art that components other than the components illustrated in FIG. 1 may be further included in the neural network apparatus 100.

The processor 110 controls overall functions for operating the neural network apparatus 100. For example, the processor 110 overall controls the neural network apparatus 100 by executing programs stored in the memory 120 in the neural network apparatus 100. The processor 110 may be implemented as, but is not limited to, a central processing unit (CPU), a graphics processing unit (GPU), an application processor (AP), or the like provided in the neural network apparatus 100.

The memory 120 is hardware for storing various data processed in the neural network apparatus 100, and may store, for example, data that was processed or that is to be processed in the neural network apparatus 100. Furthermore, the memory 120 may store applications, drivers, and the like, to be driven by the neural network apparatus 100. The memory 120 may include random access memory (RAM) such as dynamic RAM (DRAM), static RAM (SRAM), or the like, read-only memory (ROM), electrically erasable programmable read-only memory (EEPROM), CD-ROM, Blu-ray or other optical disc storages, a hard disk drive (HDD), a solid state drive (SSD), or a flash memory.

Furthermore, structural feature values and property values are matched and stored as single sets in the memory 120, and the neural network apparatus 100 may read structural feature values and property values from the memory 120 or may record structural feature values and property values in the memory 120. The property value represents characteristics of a material, and may include a real number value measured through an experiment or calculated through a simulation. Furthermore, the structural feature value is an index value used for expressing a structure of a material, and may include a molecular structure fingerprint (e.g., Morgan fingerprint or ECFP) indicating whether a particular partial structure is included.

The processor 110 may operate a deep neural network (DNN), a recurrent neural network (RNN), and a conditional variational autoencoder (CVAE).

The processor 110 may train the DNN using a descriptor and a property (property value), and may determine a factor defining a relationship between the descriptor and the property during the training. By operating the trained DNN, the processor 110 may perform a computation using a descriptor as input data in an input layer and may generate a property value as output data on the basis of a result of performing the computation.

The processor 110 may train the RNN using a descriptor and a structure (structural feature value), and may determine a factor defining a relationship between the descriptor and the structure during the training. By operating the trained RNN, the processor 110 may perform a computation using a descriptor or a factor as input data in an input layer and may generate a structural feature value as output data on the basis of a result of performing the computation.

The processor 110 may generate a new chemical structure that is not present in the database using the CVAE. In detail, a descriptor, which is high-dimensional data stored in the database, may be used as input data in an input layer of the CVAE, and an encoder may perform encoding to convert the high-dimensional descriptor into a lower-dimensional latent variable. Thereafter, a decoder of the CVAE may decode the lower-dimensional latent variable so that a descriptor, which is high-dimensional data corresponding to a new chemical structure, may be finally output from an output layer.

Furthermore, the neural network apparatus 100 may further include a user interface (not shown). The user interface represents a unit for inputting data for controlling the neural network apparatus 100. For example, the user interface may include, but is not limited to, a key pad, a dome switch, a touch pad (e.g., a capacitive type, a resistive type, an infrared sensing type, a surface acoustic wave type, an integral strain gauge type, a piezoelectric effect type, etc.), a jog wheel, a jog switch, and the like.

Hereinafter, methods of generating a chemical structure by using the neural network apparatus 100 and evaluating the generated chemical structure according to the present embodiments will be described. The methods described below may be performed by the processor 110 and the memory 120 of the neural network apparatus 100.

Figure 2:
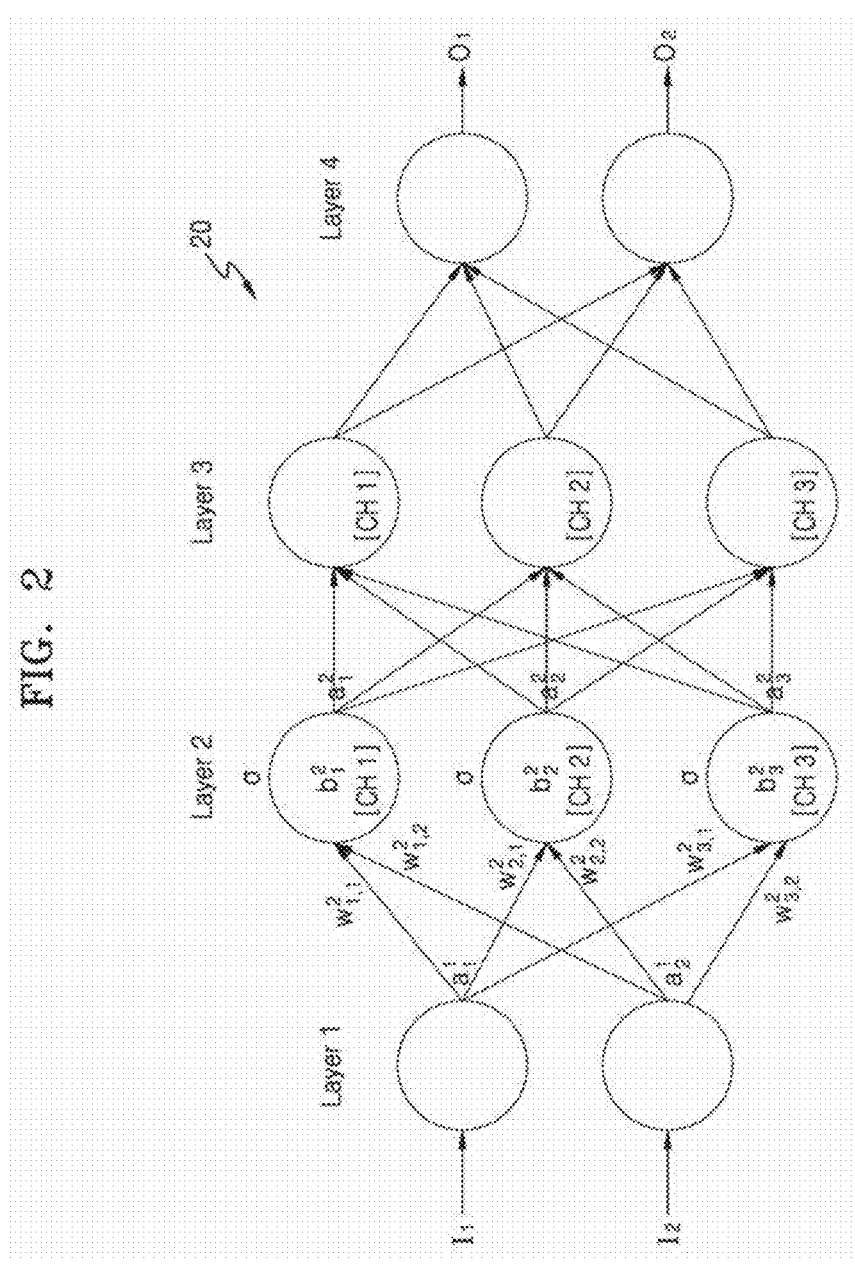
FIG. 2 is a diagram illustrating a computation performed by a deep neural network (DNN) according to an embodiment.

FIG. 2 is a diagram illustrating a computation performed by a DNN according to an embodiment.

Referring to FIG. 2, a DNN 20 may have a structure including an input layer, hidden layers, and an output layer, may perform a computation on the basis of received input data (e.g., $I_1$ and $I_2$), and may generate output data (e.g., $O_1$ and $O_2$) on the basis of a result of performing the computation.

For example, as illustrated in FIG. 2, the DNN 20 may include an input layer Layer 1, two hidden layers Layer 2 and Layer 3, and an output layer Layer 4. Since the DNN 20 includes more layers capable of processing effective information, the DNN 20 may process sets of more complicated data than that for a neural network having a single layer. Although FIG. 2 illustrates the DNN 20 as including four layers, this illustration is merely an example, and thus the DNN 20 may include more or fewer layers or more or fewer channels. That is, the DNN 20 may include layers having various structures different from those illustrated in FIG. 2.

Each of the layers included in the DNN 20 may include a plurality of channels. The channel may correspond to a neuron, a processing element (PE) unit, or a plurality of artificial nodes known to be similar thereto. For example, as illustrated in FIG. 2, the input layer Layer 1 may include two channels (or nodes), and each of the hidden layers Layer 2 and Layer 3 may include three channels. However, this configuration is merely an example, and thus each of the layers included in the DNN 20 may include various numbers of channels (or nodes).

The channels included in each of the layers of the DNN 20 may be connected to each other to process data. For example, one channel may receive data from other channels to perform a computation on the data and may output a computation result to other channels.

An input and output of each channel may be referred to as an input activation and an output activation, respectively. That is, the activation may be an output of one channel, and may also be a parameter corresponding to an input for channels included in a next layer. Furthermore, each channel may determine the activation thereof on the basis of weights and activations received from channels included in a previous layer. The weight is a parameter used for calculating the output activation in each channel, and may be a value allocated to a connection relationship between channels.

Each channel may receive an input to process the input through a computational unit or processing element for outputting an output activation, and the input and output of each channel may be mapped. For example, when σ is an activation function, $$w^i_{j,k}$$

denotes a weight from a kth channel included in an (i−1)th layer to a jth channel included in an ith layer, $$b^i_j$$

denotes a bias of the jth channel included in the ith layer, and $$a^i_j$$

denotes an activation of the jth channel of the ith layer, wherein the activation may be calculated using Equation 1 as below.

$$a^i_j = \sigma\left(\sum_k \left(w^i_{j,k} \times a^{i-1}_k\right) + b^i_j\right) \qquad \text{[Equation 1]}$$

As illustrated in FIG. 2, a first channel CH 1 of the second layer Layer 2 may be expressed as $$a^2_1.$$

8

Furthermore, $$a^2_1$$

may have a value of $$a^2_1 = \sigma\left(w^2_{1,1} \times a^1_1 + w^2_{1,2} \times a^1_2 + b^2_1\right)$$

according to Equation 1. However, Equation 1 is merely an example for describing an activation and a weight used for processing data in the DNN 20, and an embodiment of the present disclosure is not limited thereto. The activation may be a value obtained by passing, through a rectified linear unit (ReLU), a value obtained by applying an activation function to a sum of activations received from a previous layer.

In an embodiment, the DNN 20 may determine a factor defining a relationship between a descriptor and a property through learning with a descriptor and a property value. That is, among the layers Layer 1 to Layer 4 included in the DNN 20, the descriptor may be the input layer Layer 1, the property value may be the output layer Layer 4, and the factor may be at least one hidden layer Layer 2 and/or Layer 3.

The DNN 20 may perform a computation using the descriptor as input data in the input layer and may generate the property value as output data on the basis of a result of performing the computation.

Figure 3:
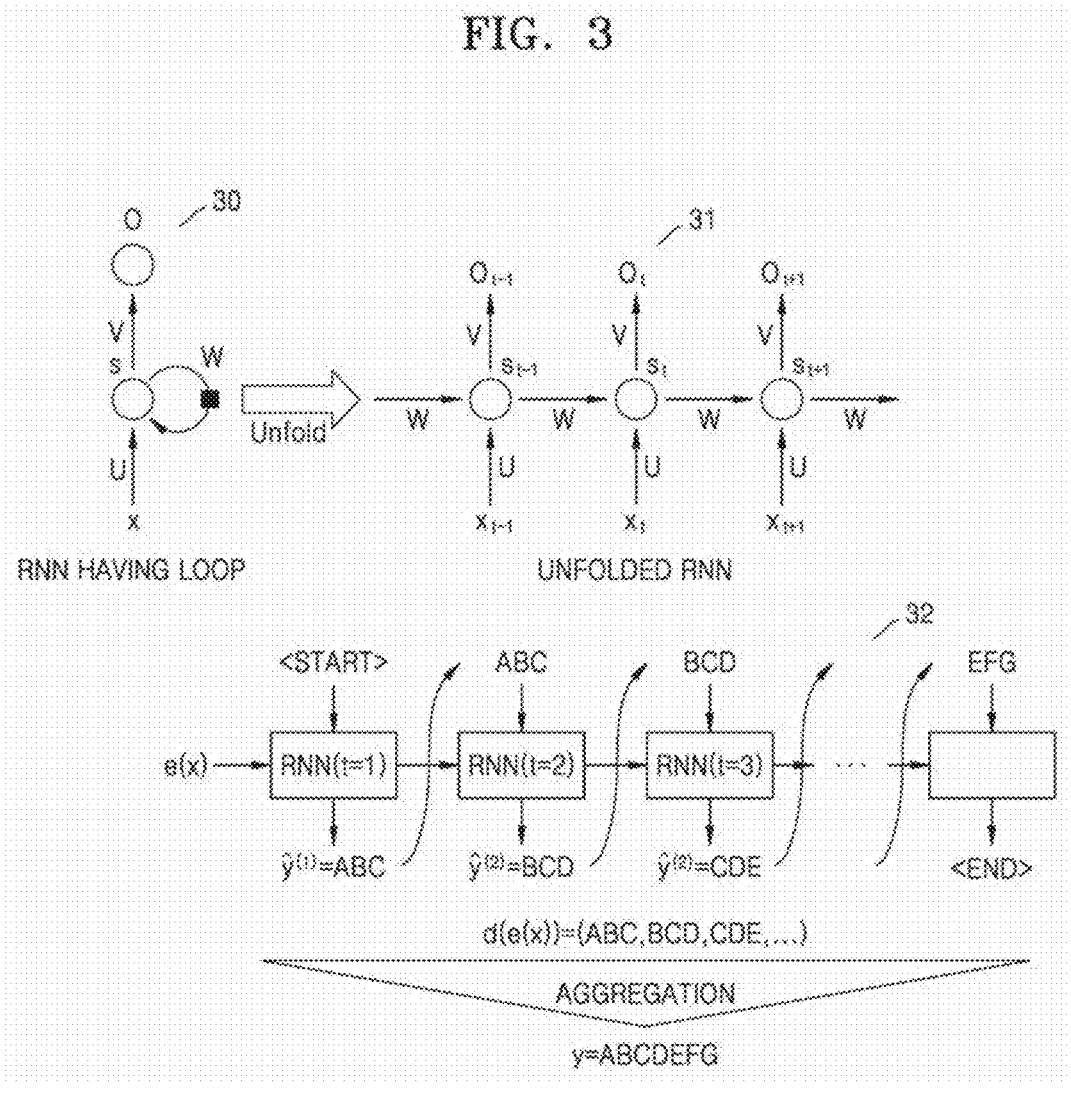
FIG. 3 is a diagram illustrating a computation performed in a recurrent neural network (RNN) according to an embodiment.

FIG. 3 is a diagram illustrating a computation performed in an RNN according to an embodiment.

For convenience, descriptions previously given with reference to FIG. 2 will be omitted.

An RNN 30 is a neural network for learning data that changes over time, such as time-series data, and is configured by connecting a network to a reference time point t and a next time point t+1. That is, the RNN 30 is a neural network configured considering an aspect of time and capable of effectively learning patterns from data that is input sequentially or given as an input of a sequence of features, by modifying a model so as to enable recursive input in a hidden layer of a neural network.

FIG. 3 illustrates a node 's' included in a hidden layer of the RNN 30. The node "s" may perform a computation on the basis of input data "x" to generate output data "o." The RNN 30 applies the same task to all sequences, and a final output result of the node "s" is affected by a previous calculation result.

An RNN 31 is achieved by unfolding the RNN 30 having a loop. "Unfolding" the RNN 30 indicates that the RNN 30 is expressed for all sequences. In the RNN 31, $x_t$ denotes an input value at a time step t, and $s_t$ denotes a hidden state at the time step t. $s_t$ may be expressed as Equation 2 as below, and, in Equation 2, tan h or Relu may be used as a function f, and $s_{t-1}$ for calculating a first hidden state may be initialized to 0 in general. Furthermore, of $o_t$ in the RNN 31 denotes an output value at the time step t.

$$s_t = f\left(U_{x_t} + W_{s_{t-1}}\right) \qquad \text{[Equation 2]}$$

$s_t$ is a memory part of a network, and contains information about events that have occurred in previous time steps, and the output value $o_t$ depends on only a memory of the current time step t.

As compared to a typical neural network structure in which each layer has different parameter values, the RNN 31 shares parameter values (U, V, and W) for all time steps. That is, in each step of the RNN 31, only input values are different and almost the same calculation is performed, and thus the number of parameters to be learned may be reduced.

In an embodiment, the RNN 32 may determine a factor defining a relationship between a descriptor and a structure through learning with a descriptor and a structure (structural feature value). As described above with reference to FIG. 2, the factor may be at least one hidden layer. The RNN 32 may perform a computation using the descriptor or the factor as input data in an input layer and may generate the structural feature value as output data on the basis of a result of performing the computation.

For example, when a character string indicating the structural feature value is "ABCDEFG," an input and output of each time step may be "ABC," "BCD," "CDE," "DEF," and "EFG". That is, in each step of an RNN part, a next character string of a character string input at a time t may be used as an input at a time t+1.

The RNN 32 may learn data (h, s) (i.e., factor and structure data) so as to maximize a generation probability of a character string indicating the structure 's'. A generation probability 'p' of a character string may be expressed as Equation 3 as below.

$$p(y|e(x))) = \prod_{t=1}^{T} p\left(y^{(t)}\middle|e(x), y^{(1)}, \ldots, y^{(t-1)}\right) \qquad \text{[Equation 3]}$$

When a configuration of an RNN part is completed through learning (i.e., when a parameter value of an RNN model used for determining a structural factor is determined), a factor obtained by encoding a descriptor may be decoded. According to another embodiment, decoding is sequentially performed in a manner in which a first part (ABC) of a decoded character string is obtained using a factor e(x) as an input, a character string "BCD" is obtained using the obtained character string "ABC" as an input, and a character string "CDE" is obtained using the obtained character string "BCD" as an input.

Referring to FIG. 3, two front characters in a character string at a specific time point t are the same as two rear characters in a character string at a time point t−1. Thereafter, character strings of each time point are aggregated so that one character string (ABCDEFG) is output.

Figure 4:
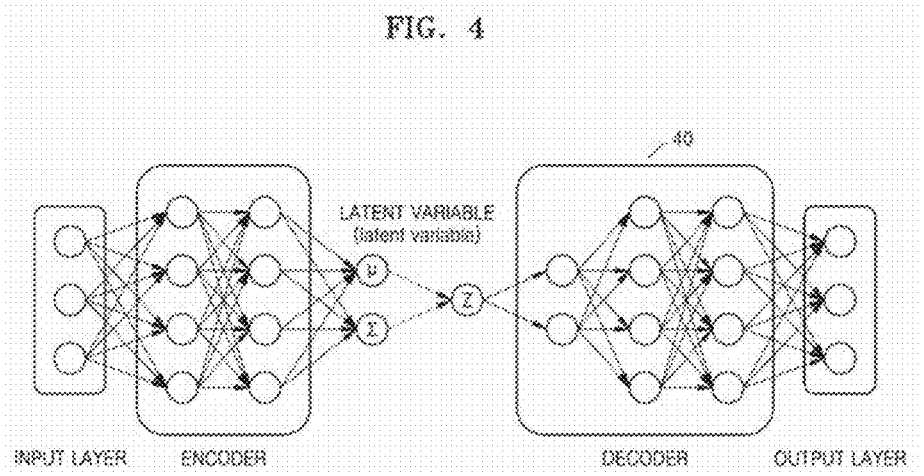
FIG. 4 is a diagram illustrating a computation performed by a conditional variational autoencoder (CVAE) according to an embodiment.

FIG. 4 is a diagram illustrating a computation performed by a CVAE according to an embodiment.

Referring to FIG. 4, a CVAE 40 has a structure including an input layer, an encoder, a decoder, and an output layer. High-dimensional data such as an image stored in a database is used as input data in the input layer of the CVAE 40, and encoding is performed in the encoder of the CVAE 40 to convert the high-dimensional input data into a lower-dimensional latent variable z. In an embodiment, the latent variable z follows a normal distribution with a mean μ and a variance σ, and may be 2 to 50-dimensional data. Thereafter, the decoder may decode the lower-dimensional latent variable z so that the output layer may output a new image (high-dimensional data), which is not present in the database.

For example, the latent variable may include a shape of an object, a camera view point, information about a light source, or the like, when an image of a person is used as the input data, and the latent variable may include an angle of a line, an aspect ratio, or the like, when a number image is used as the input data.

Furthermore, the latent variable z may be mapped to a latent map. Here, new data, which is not present in the database, may be generated in the output layer by inputting, to the decoder, a predetermined value z' included in a region in which the latent variable z is not mapped in the latent map and decoding the predetermined value z'.

In the CVAE 40, a descriptor, which is high-dimensional data stored in the database, may be used as input data in the input layer, and the encoder may perform encoding to convert the high-dimensional descriptor into a lower-dimensional latent variable. Thereafter, the decoder of the CVAE 40 may decode the lower-dimensional latent variable so that a descriptor, which is high-dimensional data corresponding to a new chemical structure, may be finally output from the output layer.

Figure 5:
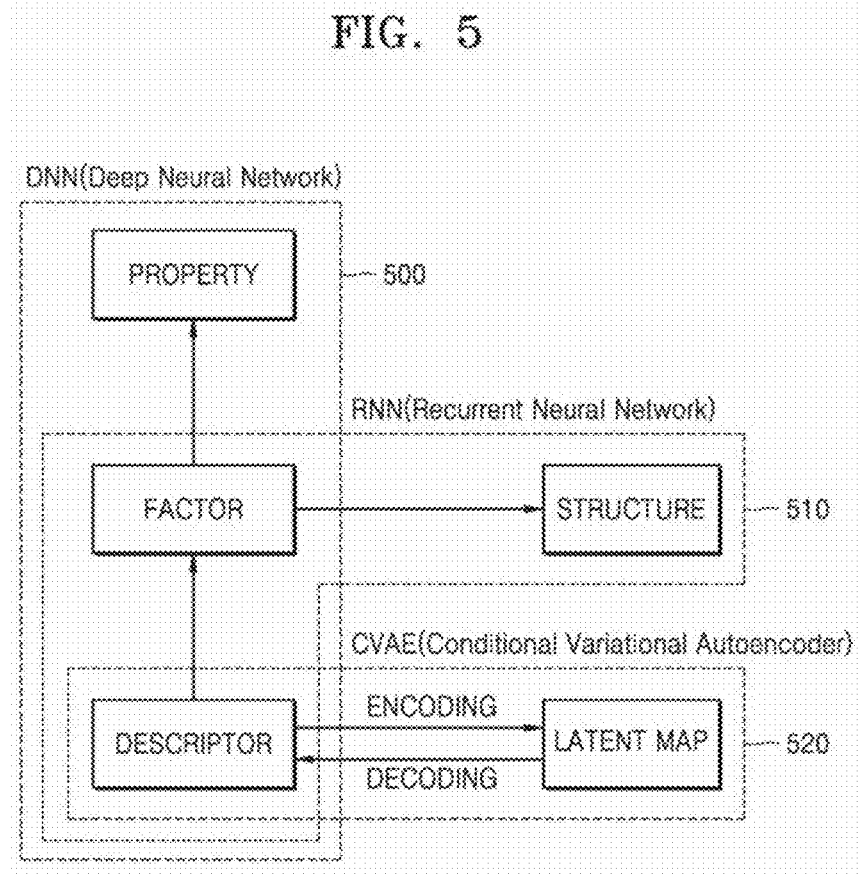
FIG. 5 is a conceptual diagram illustrating a neural network system for generating a chemical structure according to an embodiment.

FIG. 5 is a conceptual diagram illustrating a neural network system for generating a chemical structure according to an embodiment.

FIG. 5 illustrates a neural network system for generating a chemical structure using a DNN 500, an RNN 510, and a CVAE 520.

A descriptor, which is data used in the neural network system, may include a QSPR descriptor including immediately calculable values such as a molecular structure fingerprint (e.g., a Morgan fingerprint or ECFP) indicating whether a particular partial structure is included. The property represents characteristics of a material, and may include a real number value measured through an experiment or calculated through a simulation. The structure represents an atomic-level structure of a material. A character string format for expressing the structure may include a SMILES code, a SMARTS code, or an InChi code. For example, a structural formula may be expressed as Equation 4 according to the SMILES code, or may be expressed as Equation 5 according to the SMARTS code.

$$OC1 = C(C = C2C = CNC2 = C1)C1 = \qquad \text{[Equation 4]}$$
$$C(C = CC = C1)C1 = C2 = C(NC = C2)C = C1$$

$$[\#6] - 1 - [\#6] = [\#6] - [\#6] - 2 = [\#6] - 1 - [\#6] - \qquad \text{[Equation 5]}$$
$$1 = [\#6](-[\#6] - [\#6] = [\#7] - [\#6] - 1) - [\#7] = [\#6] - 2$$

The factor represents an element defining a relationship between the descriptor, the property, and the structure. The factor may be at least one hidden layer. When the factor includes a plurality of hidden layers, the factor defining the relationship between the descriptor and the property and the factor defining the relationship between the descriptor and the structure may be determined for each hidden layer.

The latent map may include visualizable coordinates in which two or three dimensionally expressed descriptors are mapped. Similarity between descriptors may be visualized and confirmed using the latent map.

The DNN 500 may perform a computation using the descriptor as input data in the input layer and may generate the property (or property value) as output data on the basis of a result of performing the computation. The RNN 510 may perform a computation using the descriptor or the factor as input data in the input layer and may generate the structure (or structural feature value) as output data on the basis of a result of performing the computation. The SMILES code and the SMARTS code may be used as a character string format indicating the structural feature value.

Furthermore, the DNN 500 and the RNN 510 may be trained on the basis of the relationship between the property (or property value) and the structure (or structural feature value) stored in a memory to determine the factor, which is an element defining the relationship between the descriptor, the property, and the structure. In an embodiment, the factor may be at least one hidden layer. When the factor includes a plurality of hidden layers, the factor defining the relationship between the descriptor and the property and the factor defining the relationship between the descriptor and the structure may be determined for each hidden layer.

The RNN 510 may perform a computation using the factor determined in the DNN 500 part as input data and may generate the structural feature value as output data on the basis of a result of performing the computation.

In the CVAE 520, a descriptor, which is high-dimensional data stored in the database, is used as input data in the input layer, and the encoder performs encoding to convert the high-dimensional descriptor into a lower-dimensional latent variable. Thereafter, the decoder decodes the lower-dimensional latent variable so that a descriptor, which is high-dimensional data corresponding to a new chemical structure, is output from the output layer. The property value may be generated when the descriptor output from the CVAE 520 is used as input data for the DNN 500, and the structural feature value may be generated when the output descriptor is used as input data for the RNN 510.

Figure 6:
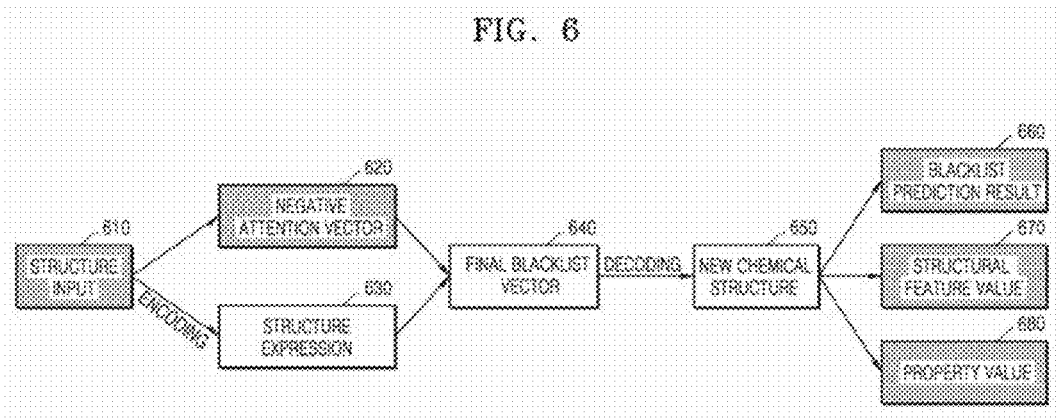
FIG. 6 is a diagram for describing a process of generating a new chemical structure using a final blacklist vector according to an embodiment.

FIG. 6 is a diagram for describing a process of generating a new chemical structure using a final blacklist vector.

A neural network apparatus may use a blacklist in a training and inference process of a chemical structure generation model.

Referring to FIG. 6, the neural network apparatus may receive a structure input 610 of a chemical structure. In an embodiment, the neural network apparatus may receive a descriptor of a specific chemical structure as the structure input 610. The descriptor may include a QSPR descriptor including immediately calculable values such as a molecular weight or the number of partial structures (e.g., rings) included in a molecular structure or a molecular structure fingerprint (e.g., Morgan fingerprint or ECFP). For example, the structure input 610 may be a 4000-dimensional vector including 0 or 1.

The neural network apparatus may receive the blacklist. The blacklist represents a partial structure, which is unfavorable for synthesis and performance. In detail, a chemical structure to be newly generated through the neural network apparatus has a property value for a specific property (e.g., transmission wavelength, light emission wavelength, etc.). Here, the neural network apparatus may be intended to generate a new chemical structure having a property value suitable for a target property value (e.g., "light emission wavelength $\lambda$=350 nm"). Here, when a partial structure corresponding to the blacklist is included in a new chemical structure, it may be highly likely that the property value of the new chemical structure is not suitable for the target property value.

Figure 7:
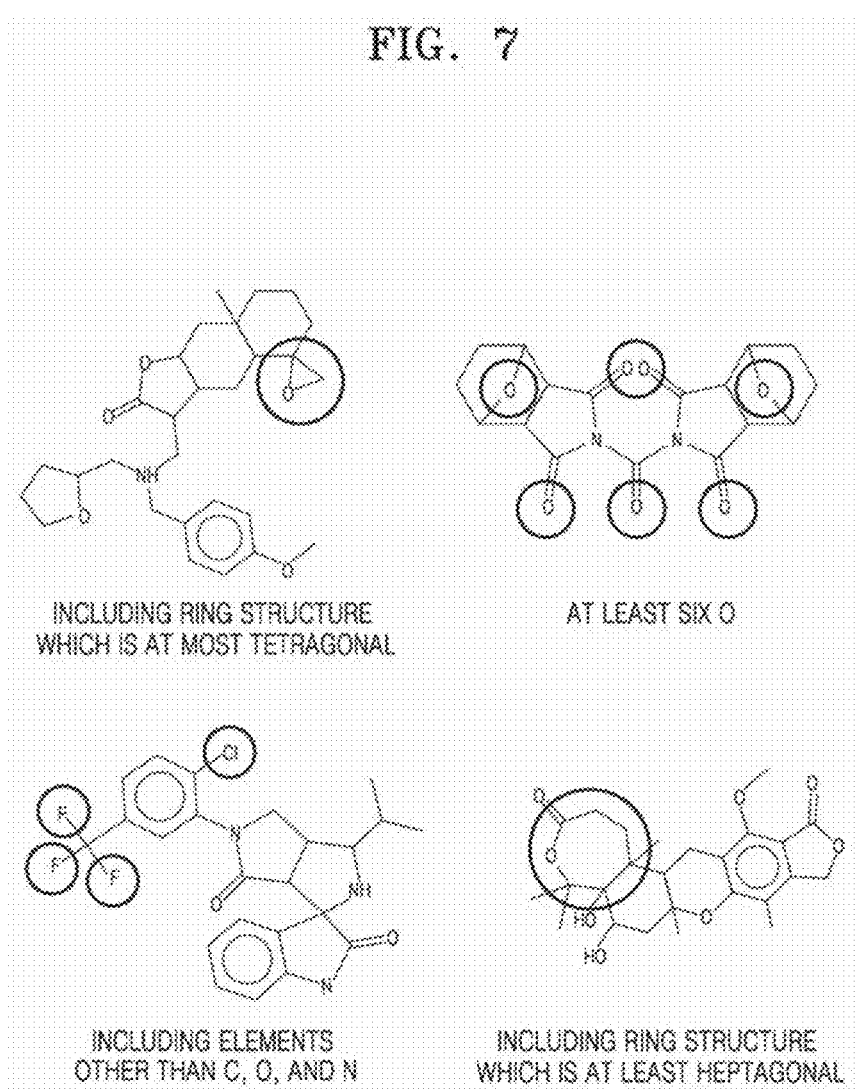
FIG. 7 shows diagrams illustrating examples of a blacklist according to an embodiment.

FIG. 7 illustrates an example of a blacklist according to an embodiment. For example, the blacklist may include the cases of "including a ring structure which is at most tetragonal," "at least six O," "including elements other than C, O, and N," "including a ring structure which is at least heptagonal," and the like. However, the blacklist is not limited to the above example, and may be variously set according to desired synthesis and performance.

The neural network apparatus may generate, on the basis of the structure input 610, a negative attention vector 620 in which the probability of presence of each of a plurality of blacklists in the structure input 610 is indicated.

A size of the negative attention vector 620 may be determined according to the number of blacklists. Furthermore, each element of the negative attention vector 620 may have a value between 0 and 1 and may indicate the probability that a corresponding blacklist will be present in the structure input 610.

For example, when four blacklists are configured as illustrated in FIG. 7, the negative attention vector 620 may be a four-dimensional vector [0.9 0.1 0.2 0.1]. This case may indicate that the probability (0.9) that the structure input 610 will correspond to the case of "including a ring structure which is at most tetragonal" is high and the probability that the structure input 610 will correspond to the other blacklists is low.

Furthermore, the neural network apparatus may generate a structure expression 630 by encoding the structure input 610. In an embodiment, the neural network apparatus may encode the structure input 610 into the structure expression 630 using the encoder of the CVAE. For example, the neural network apparatus may encode the structure input 610, which is a 4000-dimensional vector, into the structure expression 630, which is a 128-dimensional vector.

The neural network apparatus may generate a final blacklist vector 640 including a plurality of blacklists through a computation between the negative attention vector 620 and the structure expression 630. In an embodiment, the neural network apparatus may generate the final blacklist vector 640 through an element-wise computation between the negative attention vector 620 and the structure expression 630.

The neural network apparatus may generate a new chemical structure 650 by decoding the final blacklist vector 640. In an embodiment, the neural network apparatus may decode the final blacklist vector 640 into the new chemical structure 650 using the decoder of the CVAE. The new chemical structure 650 may be expressed as a descriptor.

The chemical structure generation model of the neural network apparatus may be trained using the final blacklist vector 640. In detail, the neural network apparatus may generate the new chemical structure 650 by decoding the final blacklist vector 640. The neural network apparatus may analyze the new chemical structure 650 to determine whether a blacklist having a high probability of presence in the structure input 610 is also included in the new chemical structure 650. That is, the neural network apparatus may generate a blacklist prediction result 660 by analyzing the new chemical structure 650.

The chemical structure generation model of the neural network apparatus may be trained by receiving, as feedback, the new chemical structure 650 generated from the final blacklist vector 640 and the blacklist prediction result 660 corresponding to the new chemical structure 650.

Furthermore, the neural network apparatus may input the new chemical structure 650 to an RNN and may obtain a structural feature value 670 of the new chemical structure 650 as an output value of the RNN.

The structural feature value 670 is an index value used for expressing a structure of a material, and may include a molecular structure fingerprint (e.g., Morgan fingerprint or ECFP).

Furthermore, the neural network apparatus may input the new chemical structure 650 to a DNN and may obtain a property value 680 of the new chemical structure 650 as an output value of the DNN.

The property value 680 represents a numerical value of a specific property of the new chemical structure 650. For example, the property value 680 may include a refractive index value, a modulus of elasticity, a melting point, a transmission wavelength, and a light emission wavelength.

When calculating the blacklist prediction result 660 by analyzing the new chemical structure 650, the neural network apparatus may use a non-negative parameter to calculate the blacklist prediction result 660 corresponding to the new chemical structure 650. Using a non-negative parameter indicates that a limiting condition is set so that all of parameters used in the neural network apparatus do not have negative values. For example, when a specific parameter has a negative value, the neural network apparatus may apply the specific parameter to an exponential function to convert the specific parameter into a non-negative value.

The chemical structure generation model receives, as feedback, the blacklist prediction result calculated using a non-negative parameter, and thus, the learning performance of the chemical structure generation model may be improved.

Furthermore, during a learning process of the chemical structure generation model, the neural network apparatus may receive, as the structure input 610, only chemical structures confirmed not to include at least a part of a plurality of blacklists. For example, when the number of blacklists is 13, the neural network apparatus may receive, as the structure input 610, only chemical structures not having all of the 13 blacklists. As described above, the chemical structure generation model receives, as the structure input 610, only specific chemical structures not including at least a part of blacklists, and thus, the learning performance of the chemical structure generation model may be improved.

Figure 8:
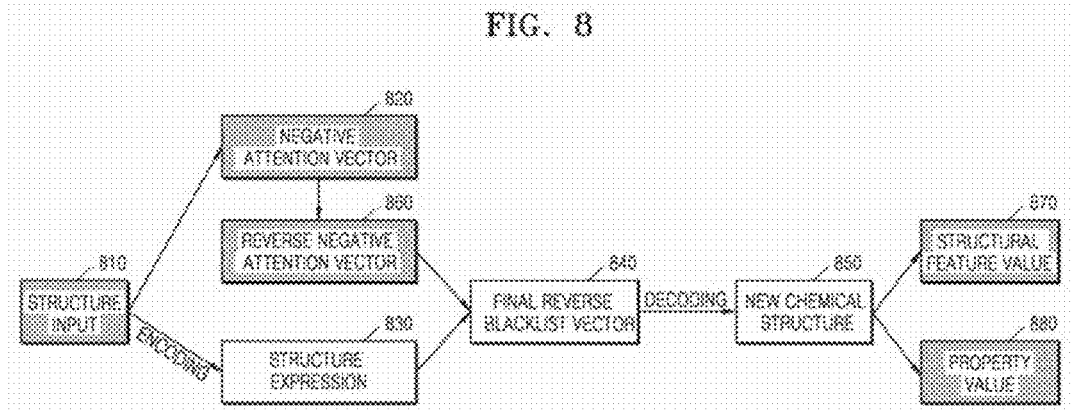
FIG. 8 is a diagram for describing a process of generating a new chemical structure using a final reverse blacklist vector according to an embodiment.

FIG. 8 is a diagram for describing a process of generating a new chemical structure using a final reverse blacklist vector.

Referring to FIG. 8, the neural network apparatus may receive a structure input 810 of a chemical structure. In an embodiment, the neural network apparatus may receive a descriptor of a specific chemical structure as the structure input 810.

The neural network apparatus may receive a blacklist. FIG. 7 illustrates an example of the blacklist. For example, the blacklist may include the cases of "including a ring structure which is at most tetragonal," "at least six O," "including elements other than C, O, and N," "including a ring structure which is at least heptagonal," and the like. However, the blacklist is not limited to the above example, and may be variously set according to desired synthesis and performance.

The neural network apparatus may generate, on the basis of the structure input 810, a negative attention vector 820 in which the probability of presence of each of a plurality of blacklists in the structure input 810 is displayed.

A size of the negative attention vector 820 may be determined according to the number of blacklists. Furthermore, each element of the negative attention vector 820 may have a value between 0 and 1 and may indicate the probability that a corresponding blacklist will be present in the structure input 810.

For example, when four blacklists are configured as illustrated in FIG. 7, the negative attention vector 820 may be a four-dimensional vector [0.9 0.1 0.2 0.1]. In this case, it may be recognized that the probability (0.9) that the structure input 810 will correspond to the case of "including a ring structure which is at most tetragonal" is high and the probability that the structure input 810 will correspond to the other blacklists is low.

The neural network apparatus may calculate a reverse negative attention vector 860 using the negative attention vector 820. In an embodiment, the neural network apparatus may calculate a difference between a fundamental vector and the negative attention vector 820 as the reverse negative attention vector 860. Here, the fundamental vector may represent a vector having the same size as the negative attention vector 820 and having elements, all of which have a value of 1.

For example, when the negative attention vector 820 is [0.9 0.1 0.2 0.1], the reverse negative attention vector 860 is [0.1 0.9 0.8 0.9]. That is, the fact that the values of the elements of the reverse negative attention vector 860 are close to 1 indicates that it is highly likely that blacklists corresponding to the elements are not present in the structure input 810.

Furthermore, the neural network apparatus may generate a structure expression 830 by encoding the structure input 810. In an embodiment, the neural network apparatus may encode the structure input 810 into the structure expression 830 using the encoder of the CVAE.

The neural network apparatus may generate a final reverse blacklist vector 840 not including a plurality of blacklists through a computation between the reverse negative attention vector 860 and the structure expression 830. In an embodiment, the neural network apparatus may generate the final reverse blacklist vector 840 through an element-wise computation between the reverse negative attention vector 860 and the structure expression 830.

The neural network apparatus may generate a new chemical structure 850 by decoding the final reverse blacklist vector 840. In an embodiment, the neural network apparatus may decode the final reverse blacklist vector 840 into the new chemical structure 850 using the decoder of the CVAE. The new chemical structure 850 may be expressed as a descriptor.

As described above, the fact that the values of specific elements of the reverse negative attention vector 860 are close to 1 indicates that it is highly likely that blacklists corresponding to the specific elements are not present in the structure input 810. That is, it is highly likely that the new chemical structure generated on the basis of the reverse negative attention vector 860 does not include blacklists included in the structure input 810.

The blacklist represents a partial structure, which is unfavorable for synthesis and performance. Thus, when the new chemical structure 850 does not include blacklists, it is highly likely that a property value 880 of the new chemical structure 850 is suitable for a target property value.

The neural network apparatus may input the new chemical structure 850 to an RNN and may obtain a structural feature value 870 of the new chemical structure 850 as an output value of the RNN.

Furthermore, the neural network apparatus may input the new chemical structure 850 to a DNN and may obtain a property value 880 of the new chemical structure 850 as an output value of the DNN.

In an embodiment, the chemical structure generation model of the neural network apparatus may be trained using the final reverse blacklist vector 840. In detail, the neural network apparatus may generate the new chemical structure

850 by decoding the final reverse blacklist vector 840. The neural network apparatus may analyze the new chemical structure 850 to determine whether a blacklist having a high probability of presence in the structure input 810 is also included in the new chemical structure 850. That is, the neural network apparatus may generate a blacklist prediction result by analyzing the new chemical structure 850.

The chemical structure generation model of the neural network apparatus may be trained by receiving, as feedback, the new chemical structure 850 generated from the final reverse blacklist vector 840 and the blacklist prediction result corresponding to the new chemical structure 850.

Furthermore, after learning of the chemical structure generation model is completed, the neural network apparatus may select only a portion of a plurality of blacklists (hereinafter referred to as "selected blacklists") used during the learning process so as to generate the new chemical structure 850.

In detail, the neural network apparatus may generate, on the basis of the structure input 810, the negative attention vector 820 in which the probability of presence of each of the selected blacklists in the structure input 810 is indicated. For example, the neural network apparatus may change values of elements corresponding to non-selected blacklists among the elements of the negative attention vector 820 into 0, so as to substantially remove the non-selected blacklists that were not selected.

The neural network apparatus may calculate the reverse negative attention vector 860 using the negative attention vector 820. In an embodiment, the neural network apparatus may generate the final reverse blacklist vector 840, in which portions not corresponding to the selected blacklists are indicated, through an element-wise computation between the reverse negative attention vector 860 and the structure expression 830. The neural network apparatus may generate the new chemical structure 850 by decoding the final reverse blacklist vector 840.

Therefore, even when the blacklists used in the learning of the chemical structure generation model are changed at a later time (e.g., only some blacklists are used), the neural network apparatus may generate the new chemical structure 850 by using the pre-trained chemical structure generation model, without training the chemical structure generation model each time the blacklists are changed.

Figure 9:
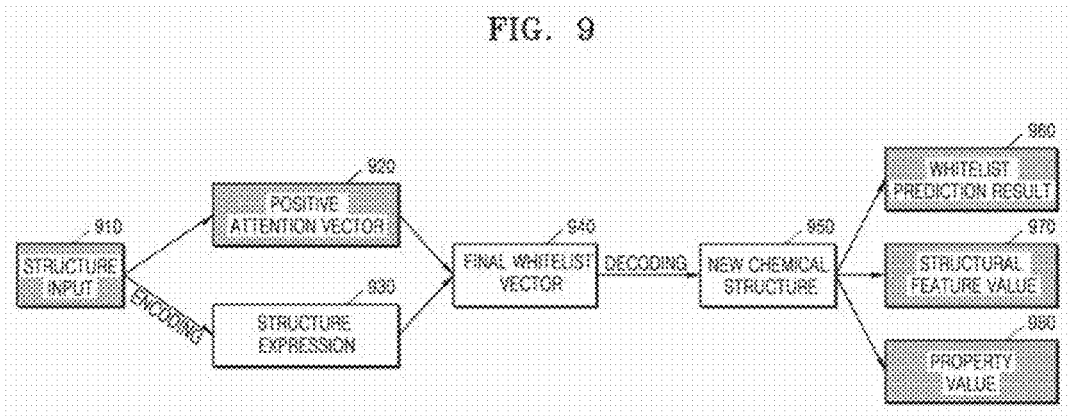
FIG. 9 is a diagram for describing a process of generating a new chemical structure using a whitelist vector according to an embodiment.

FIG. 9 is a diagram for describing a process of generating a new chemical structure using a final whitelist vector.

The neural network apparatus may use not only a blacklist but also a whitelist in a learning and inference process of the chemical structure generation model. For convenience, descriptions previously given with reference to FIG. 7 and FIG. 8 will be omitted.

Referring to the FIG. 9, the neural network apparatus may receive a structure input 910 of a chemical structure.

The neural network apparatus may receive a whitelist. The whitelist is a contrary concept of the blacklist, and represents a partial structure suitable for synthesis and performance. In detail, a chemical structure to be newly generated through the neural network apparatus has a property value for a specific property (e.g., a transmission wavelength, a light emission wavelength, etc.). Here, the neural network apparatus may be intended to generate a new chemical structure having a property value suitable for a target property value (e.g., "light emission wavelength $\lambda=350$ nm"). Here, when a partial structure corresponding to the whitelist is included in a new chemical structure, it may be highly likely that the property value of the new chemical structure is suitable for the target property value.

The neural network apparatus may generate, on the basis of the structure input 910, a positive attention vector 920 in which the probability of presence of each of a plurality of whitelists in the structure input 910 is indicated.

A size of the positive attention vector 920 may be determined according to the number of whitelists. Furthermore, each element of the positive attention vector 920 may have a value between 0 and 1 and may indicate the probability that a corresponding whitelist will be present in the structure input 910.

The neural network apparatus may generate a final whitelist vector 940 including a plurality of whitelists through a computation between the positive attention vector 920 and a structure expression 930. In an embodiment, the neural network apparatus may generate the final whitelist vector 940 through an element-wise computation between the positive attention vector 920 and the structure expression 930.

The neural network apparatus may generate a new chemical structure 950 by decoding the final whitelist vector 940.

The chemical structure generation model of the neural network apparatus may be trained using the final whitelist vector 940. In detail, the neural network apparatus may generate the new chemical structure 950 by decoding the final whitelist vector 940. The neural network apparatus may analyze the new chemical structure 950 to determine whether a whitelist having a high probability of presence in the structure input 910 is also included in the new chemical structure 950. That is, the neural network apparatus may generate a whitelist prediction result 960 by analyzing the new chemical structure 950.

The chemical structure generation model of the neural network apparatus may be trained by receiving, as feedback, the new chemical structure 950 generated from the final whitelist vector 940 and the whitelist prediction result 960 corresponding to the new chemical structure 950.

In an embodiment, during a learning process of the chemical structure generation model, the neural network apparatus may receive, as the structure input 910, only chemical structures confirmed to include at least a part of a plurality of whitelists. For example, when the number of whitelists is 13, the neural network apparatus may receive, as the structure input 910, only chemical structures having at least 10 whitelists among the 13 whitelists.

Furthermore, during the learning process of the chemical structure generation model, the neural network apparatus may receive, as the structure input 910, only chemical structures confirmed not to include at least a part of a plurality of blacklists and confirmed to include at least a part of a plurality of whitelists.

As described above, the chemical structure generation model receives, as the structure input 910, only specific chemical structures including at least a part of whitelists or specific chemical structures not including at least a part of blacklists and including at least a part of the whitelists, and thus, the learning performance of the chemical structure generation model may be improved.

Figure 10:
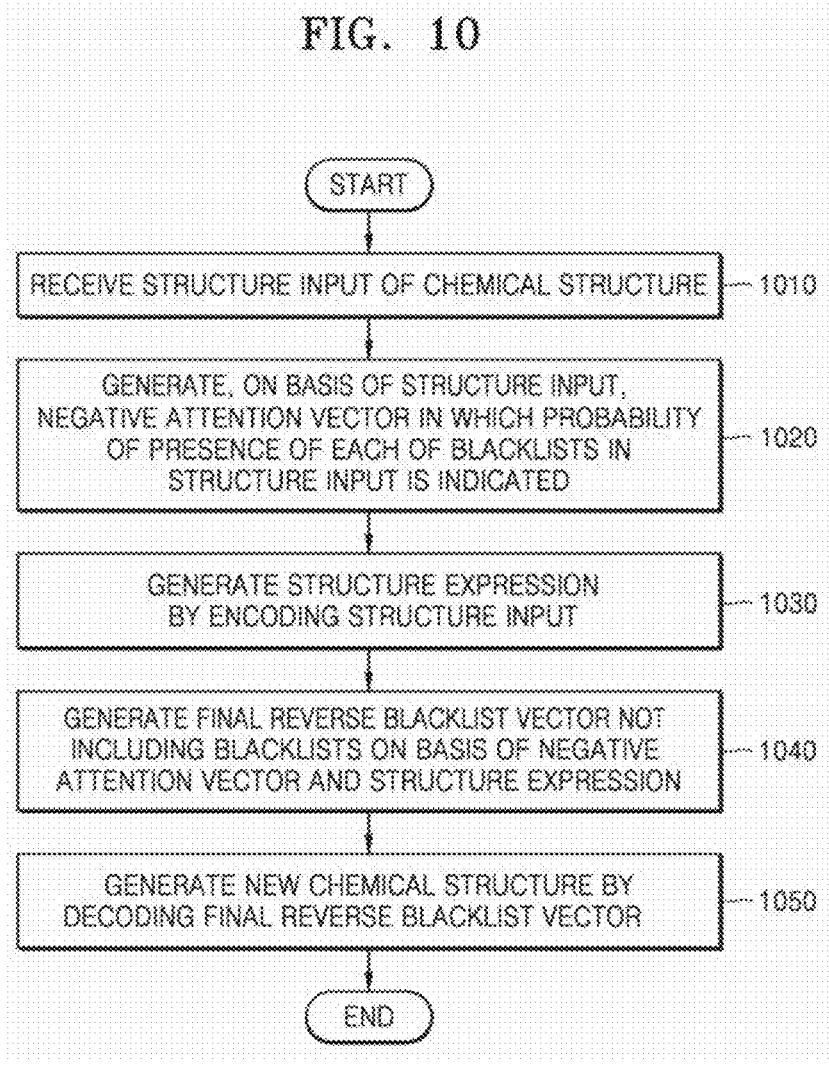
FIG. 10 is a flowchart illustrating a method, performed by a neural network apparatus, of generating a new chemical structure according to an embodiment.

FIG. 10 is a flowchart illustrating a method, performed by a neural network apparatus, of generating a new chemical structure according to an embodiment. The method of generating a chemical structure by a neural network apparatus, illustrated in FIG. 10, is related to the embodiments described above with reference to the above-mentioned drawings. Thus, although omitted below, the descriptions provided above with reference to the above-mentioned drawings may apply to the method of FIG. 10.

Referring FIG. 10, in operation 1010, the neural network apparatus may receive a structure input of a chemical structure.

In an embodiment, the neural network apparatus may receive a descriptor of a specific chemical structure as the structure input. The descriptor may include a QSPR descriptor including immediately calculable values such as a molecular weight or the number of partial structures (e.g., rings) included in a molecular structure or a molecular structure fingerprint (e.g., Morgan fingerprint or ECFP).

In operation 1020, the neural network apparatus may generate, on the basis of the structure input, a negative attention vector in which the probability of presence of each of a plurality of blacklists in the structure input is indicated.

The blacklist represents a partial structure, which is unfavorable for synthesis and performance.

A size of the negative attention vector may be determined according to the number of blacklists. Furthermore, each element of the negative attention vector may have a value between 0 and 1 and may indicate the probability that a corresponding blacklist will be present in the structure input.

In operation 1030, the neural network apparatus may generate a structure expression by encoding the structure input.

In an embodiment, the neural network apparatus may encode the structure input into the structure expression using the encoder of the CVAE.

In operation 1040, the neural network apparatus may generate a final reverse blacklist vector not including the plurality of blacklists on the basis of the negative attention vector and the structure expression.

The neural network apparatus may calculate a reverse negative attention vector using the negative attention vector. The neural network apparatus may generate the final reverse blacklist vector in which portions not corresponding to the plurality of blacklists are indicated, through a computation between the reverse negative attention vector and the structure expression. For example, the neural network apparatus may generate the final reverse blacklist vector through an element-wise multiplication between the reverse negative attention vector and the structure expression.

In operation 1050, the neural network apparatus may generate a new chemical structure by decoding the final reverse blacklist vector.

The neural network apparatus may decode the final reverse blacklist vector into the new chemical structure using the decoder of the CVAE. The new chemical structure may be expressed as a descriptor.

It is highly likely that the new chemical structure generated on the basis of the final reverse blacklist vector does not include a portion corresponding to a blacklist for the structure input. The blacklist represents a partial structure, which is unfavorable for synthesis and performance. Thus, when the new chemical structure does not include blacklists, it is highly likely that the property value of the new chemical structure is suitable for a target property value.

The neural network apparatus may input the new chemical structure to an RNN and may obtain the structural feature value of the new chemical structure as an output value of the RNN. Furthermore, the neural network apparatus may input the new chemical structure to a DNN and may obtain the property value of the new chemical structure as an output value of the DNN.

During a learning process of the chemical structure generation model, the neural network apparatus may generate a final blacklist vector including a plurality of blacklists through a computation between the negative attention vector and the structure expression. For example, the neural network apparatus may generate the final blacklist vector through an element-wise multiplication between the negative attention vector and the structure expression.

Furthermore, the neural network apparatus may train the chemical structure generation model by feeding a new chemical structure and a blacklist prediction result corresponding to the new chemical structure back to the chemical structure generation model.

The present embodiments may be implemented in the form of a non-transitory recording medium containing computer-executable instructions, such as program modules executable by a computer. The computer-readable recording medium may include any available medium accessible by a computer, and may include all of volatile and non-volatile media and detachable and non-detachable media. Furthermore, the computer-readable recording medium may include all of computer storage media and communication media. The computer storage media include all of volatile and non-volatile media and detachable and non-detachable media implemented by any method or technology for storing information such as computer-readable instructions, data structures, program modules, or other data. The communication media typically include other data of modulated data signals such as computer-readable instructions, data structures, and program modules, or other transmission mechanisms, and include any information delivery media.

Furthermore, in the present specification, the term "unit" may indicate a hardware component such as a processor or a circuit and/or a software component executed by a hardware component such as a processor.

The above description is merely illustrative, and it should be understood that those of ordinary skill in the art could make modifications without departing from the technical concept of the present disclosure. Therefore, the above embodiments should be considered illustrative and should not be construed as limiting. For example, each component described as a single type may be distributed, and likewise, components described as being distributed may be implemented as a combined form.

According to the present disclosure, a final reverse blacklist vector not including blacklists is generated using a reverse negative attention vector, and the final reverse blacklist vector is decoded, and thus, a new chemical structure not including unfavorable blacklists for synthesis may be generated.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A processor-implemented method of a neural network apparatus that includes a processor and a memory storing relationship between descriptor information, property information, and structural formula information, the method comprising:

obtaining a trained chemical structure generation model by operating a conditional variational autoencoder (CVAE), a deep neural network (DNN) and a recurrent neural network (RNN) together, the CVAE comprising an encoder and a decoder;

receiving, by the encoder of the CV AE, a high-dimensional descriptor of a structure input of a chemical structure as structure information;

performing, by the encoder of the CV AE, an encoding operation to convert the high-dimensional descriptor into a lower-dimensional latent variable;

performing, by the decoder of the CV AE, a decoding operation to decode the lower-dimensional latent variable to generate descriptor information, which is high-dimensional data corresponding to a new chemical structure expression;

performing a first training operation to train the DNN based on the descriptor information and property information to obtain a factor defining a relationship between the descriptor information and the property information, and performing a second training operation to train the RNN based on the structure information and at least one of the descriptor information or the factor obtained in the first training operation;

generating, based on the structure input, a negative attention vector comprising a plurality of first elements, each of the plurality of first elements corresponding to one of a plurality of blacklists, and each of the plurality of first elements indicating a probability that the corresponding one of the plurality of blacklists is present in the structure input;

generating a reverse negative attention vector based on a difference between a fundamental vector and the negative attention vector, the fundamental vector representing a vector having a same size as the negative attention vector and having elements, all of which have a value of 1;

generating a final reverse blacklist vector based on an element-wise multiplication between the reverse negative attention vector and the structure expression, the final reverse blacklist vector not including the plurality of blacklists;

generating, by decoding the final reverse blacklist vector using the decoder of the trained chemical structure generation model, a new chemical structure expression that does not include the plurality of blacklists;

generating a final blacklist vector comprising the plurality of blacklists based on the negative attention vector and the structure expression during the obtaining of the trained chemical structure generation model;

iteratively performing the first and the second training operations to obtain an updated trained chemical structure generation model based on the new chemical structure expression and a blacklist prediction result corresponding to the new chemical structure expression; and outputting the new chemical structure expression that does not include the plurality of blacklists, wherein the DNN comprises a plurality of layers including an input layer, one or more hidden layers and an output layer, wherein each of the plurality of layers comprises a plurality of channels, wherein each of the plurality of channels comprises a processing element, wherein the descriptor information is provided in the input layer, the property information is provided in the output layer, the factor may be provided in the one or more hidden layers, wherein the structure information comprises a character string, wherein, in each step of the RNN, a subsequent part of the character string, following a current part of the character string input at a time t, is used as an input at a time t+1, wherein the RNN is trained using the factor obtained from the DNN so that the new chemical structure expression reflects the relationship between the descriptor information and the property information defined by the DNN.

2. The method of claim 1, further comprising:

calculating the blacklist prediction result using a non-negative parameter.

3. The method of claim 1, wherein the structure input includes chemical structures confirmed not to include at least one of the plurality of blacklists during a learning process of the trained chemical structure generation model.

4. The method of claim 1, further comprising:

selecting one or more of the plurality of blacklists, wherein the generating of the negative attention vector comprises generating, based on the structure input, the negative attention vector in which the respective probability of presence of each of the selected blacklists in the structure input is indicated, and wherein the generating of the final reverse blacklist vector comprises generating the final reverse blacklist vector that does not include the selected blacklists based on the negative attention vector and the structure expression.

5. The method of claim 1, further comprising:

generating, based on the structure input, a positive attention vector comprising a plurality of second elements, each of the plurality of second elements corresponding to one of a plurality of whitelists, and each of the plurality of second elements indicating a probability that the corresponding one of the plurality of whitelists is present in the structure input;

generating a final whitelist vector including the plurality of whitelists based on the positive attention vector and the structure expression; and generating the new chemical structure by decoding the final whitelist vector.

6. The method of claim 5, wherein the structure input includes chemical structures confirmed to include at least one of the plurality of whitelists during a learning process of the trained chemical structure generation model.

7. The method of claim 5, wherein the structure input includes chemical structures confirmed not to include at least one of the plurality of blacklists, and confirmed to include at least one of the plurality of whitelists during a learning process of the trained chemical structure generation model.

8. A neural network apparatus for generating a new chemical structure expression, the neural network apparatus comprising:

a memory configured to store relationship between descriptor information, property information, and structural formula information; and a processor configured to:

obtain a trained chemical structure generation model by operating a conditional variational autoencoder (CVAE), a deep neural network (DNN) and a recurrent neural network (RNN) together, the CVAE comprising an encoder and a decoder;

receive, by the encoder of the CV AE, a high-dimensional descriptor of a structure input of a chemical structure as structure information;

perform, by the encoder of the CV AE, an encoding operation to convert the high-dimensional descriptor into a lower-dimensional latent variable;

perform, by the decoder of the CV AE, a decoding operation to decode the lower-dimensional latent variable to generate descriptor information, which is high-dimensional data corresponding to a new chemical structure expression;

perform a first training operation to train the DNN based on the descriptor information and property information to obtain a factor defining a relationship between the descriptor information and the property information, and perform a second training operation to train the RNN based on the structure information and at least one of the descriptor information or the factor obtained in the first training operation;

generate, based on the structure input, a negative attention vector comprising a plurality of first elements, each of the plurality of first elements corresponding to one of a plurality of blacklists, and each of the plurality of first elements indicating a probability that the corresponding one of the plurality of blacklists is present in the structure input;

generating a reverse negative attention vector based on a difference between a fundamental vector and the negative attention vector, the fundamental vector representing a vector having a same size as the negative attention vector and having elements, all of which have a value of 1;

generate a final reverse blacklist vector based on an element-wise multiplication between the reverse negative attention vector and the structure expression, the final reverse blacklist vector not including the plurality of blacklists;

generate, by decoding the final reverse blacklist vector using the decoder of the trained chemical structure generation model, a new chemical structure expression that does not include the plurality of blacklists;

generate a final blacklist vector comprising the plurality of blacklists based on the negative attention vector and the structure expression during the obtaining of the trained chemical structure generation model;

iteratively perform the first and the second training operations to obtain an updated trained chemical structure generation model based on the new chemical structure expression and a blacklist prediction result corresponding to the new chemical structure expression; and output the new chemical structure expression that does not include the plurality of blacklists, wherein the DNN comprises a plurality of layers including an input layer, one or more hidden layers and an output layer, wherein each of the plurality of layers comprises a plurality of channels, wherein each of the plurality of channels comprises a processing element, wherein the descriptor information is provided in the input layer, the property information is provided in the output layer, the factor may be provided in the one or more hidden layers, wherein the structure information comprises a character string, wherein, in each step of the RNN, a subsequent part of the character string, following a current part of the character string input at a time t, is used as an input at a time t+1, wherein the RNN is trained using the factor obtained from the DNN so that the new chemical structure expression reflects the relationship between the descriptor information and the property information defined by the DNN.

9. The neural network apparatus of claim 8, wherein the processor is further configured to:

calculate the blacklist prediction result using a non-negative parameter.

10. The neural network apparatus of claim 8, wherein the structure input includes chemical structures confirmed not to include at least one of the plurality of blacklists during a learning process of the trained chemical structure generation model.

11. The neural network apparatus of claim 8, wherein the processor is further configured to:

select one or more of the plurality of blacklists;

generate, based on the structure input, the negative attention vector that indicates a respective probability of presence of each of the selected blacklists in the structure input; and generate the final reverse blacklist vector that does not include the selected blacklists based on the negative attention vector and the structure expression.

12. The neural network apparatus of claim 8, wherein the processor is further configured to:

generate, based on the structure input, a positive attention vector comprising a plurality of second elements, each of the plurality of second elements corresponding to one of a plurality of whitelists, and each of the plurality of second elements indicating a probability that the corresponding one of the plurality of whitelists is present in the structure input;

generate a final whitelist vector that indicates portions corresponding to the plurality of whitelists, based on the positive attention vector and the structure expression; and generate the new chemical structure by decoding the final whitelist vector.

13. The neural network apparatus of claim 12, wherein the structure input includes chemical structures confirmed to include at least one of the plurality of whitelists during a learning process of the trained chemical structure generation model.

14. The neural network apparatus of claim 12, wherein the structure input includes chemical structures confirmed not to include at least one of the plurality of blacklists and confirmed to include at least one of the plurality of whitelists during a learning process of the trained chemical structure generation model.

15. A non-transitory computer-readable storage medium storing instructions that, when executed by a processor, configure the processor to perform the method of claim 1.

* * * * *